(12) United States Patent
Ruth et al.

(10) Patent No.: US 6,489,421 B1
(45) Date of Patent: Dec. 3, 2002

(54) QUATERNARY AMMONIUM POLYMER, ITS PREPARATION, ITS USE FOR SEPARATING BIOMOLECULES

(75) Inventors: Freitag Ruth, St-Sulpice; Wandrey Christine, Lausanne, both of (CH)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 0 days.

(21) Appl. No.: 09/646,501

(22) PCT Filed: Mar. 18, 1999

(86) PCT No.: PCT/IB99/00455

§ 371 (c)(1),
(2), (4) Date: Sep. 18, 2000

(87) PCT Pub. No.: WO99/47574

PCT Pub. Date: Sep. 23, 1999

(30) Foreign Application Priority Data

Mar. 18, 1998 (EP) .............................................. 98810231

(51) Int. Cl.$^7$ ............................................. C08F 126/06
(52) U.S. Cl. ........................ 526/258; 526/310; 526/312
(58) Field of Search ................................. 526/258, 310, 526/312

(56) References Cited

U.S. PATENT DOCUMENTS

| | | | | |
|---|---|---|---|---|
| 4,064,333 A | * | 12/1977 | Rabinowitz et al. ........... | 526/77 |
| 4,357,207 A | | 11/1982 | Yorke | |
| 5,667,697 A | * | 9/1997 | Salmen et al. ............... | 210/727 |
| 5,840,158 A | * | 11/1998 | Choo et al. ............... | 162/164.3 |

FOREIGN PATENT DOCUMENTS

| | | |
|---|---|---|
| DD | 246 680 A3 | 6/1987 |
| DE | 37 43 742 A1 | 7/1989 |

OTHER PUBLICATIONS

R. Freitag et al., "Displacement chromotography in biotechnical downstream processing," Journal of Chromatography A, 691 (1995) 101–112.

G. Jayaraman et al., "Ion–exchange displacement chromotography of proteins; Dentritic polymer as novel displacers," Journal of Chromatography A, 702 (1995) 143–155.

C.S. Patrickios et al., "Block Methacrylic Polyampholytes as protein Displacers in Ion–Exchange Chromatography," Biotechnol. Prog., 1995, 11, 33–38.

C. Wandrey et al., "Diallyldimethylammonium Chloride and its Polymers," Advances in Polymer Science, (1999) vol. 145, 123–182.

Terabe et al., J. Chromatography, 515 (1990), 667–676.*

De et al., AIChE J., 43(10), 1997, 2415–2423.*

* cited by examiner

*Primary Examiner*—Helen L. Pezzuto
(74) *Attorney, Agent, or Firm*—Clifford W. Browning; Woodard, Emhardt, Naughton, Moriarty & McNett

(57) ABSTRACT

A linear water-soluble quaternary ammonium polymer having a homopolymeric chain of repeating unit of general formula (I):

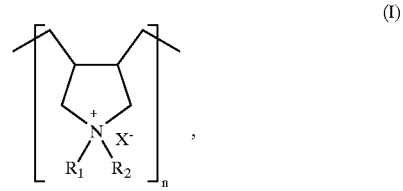

where each of $R_1$ and $R_2$ independently represents a member selected from the group consisting of linear or branched alkyl, hydroxyalkyl, alkoxyalkyl groups having from 1 to 6 carbon atoms, $X^-$ represents an anion and n is an integer comprised between 30 and 220 has been prepared. Furthermore, the polymer has a molar mass distribution of less than or equal to 1.5. The polymer is used as a displacer in a displacement mode of chromatography.

11 Claims, 6 Drawing Sheets

QUATERNARY AMMONIUM POLYMER, ITS PREPARATION, ITS USE FOR SEPARATING BIOMOLECULES

The present invention relates to a linear water-soluble quaternary ammonium polymer, a process for the preparation of this polymer, the use of this polymer as a displacer in the displacement mode of chromatography and a method for separating biomolecules through the displacement mode chromatography using this polymer.

The majority of the separation or isolation procedures used in the pharmaceutical field, or other related fields such as the biochemical, the biotechnological and the chemical fields, rely on chromatography, i.e. a differential separation between two phases, a stationary one (usually solid) and a mobile one (usually fluid).

Elution mode chromatography is the most commonly used mode of chromatography. In this method, the sample containing different components to be separated is adsorbed on the stationary phase. The mobile phase, called eluent, is chosen such that the components bind reversibly onto the stationary phase. As the eluent is flowing over the stationary phase, the different components migrate along the column at a speed which reflects their relative affinity for the stationary phase.

Biomolecules such as proteins are generally purified by gradient elution mode chromatography using ion-exchange adsorbents as stationary phase. The elution involves changing the pH of the buffer solution passing through the column or, more common, increasing the salt concentration in the buffer solution passing through the column. When the pH of the solution is changed, the electric charges on the proteins or the ion-exchange adsorbent material are changed and the proteins are released. With an increase of the salt concentration, the salts weaken the bonds between the proteins and the ion-exchange adsorbent material to release the proteins. As the salt level is gradually increased, the proteins having the smaller number of charges, respectively the lower charge density (mass to charge ratio) will generally be released and eluted first and those with the larger number of charges, respectively the higher charge density, will be released later.

Displacement chromatography is a special mode of chromatography. The basic principle of chromatography still applies, but in this case the driving force behind the separation is the push of an advancing front of a so-called displacer, rather than the (increasing) elution strength of a mobile phase. Under the influence of an advancing displacer front, the substance mixture is resolved into consecutive zones of the pure substances.

The displacer is a substance with a higher binding affinity to the stationary phase than the components to be separated. As the displacer front advances, the number of stationary sites available to the binding components are continuously decreased, which engenders competition for the binding sites between the displacer and the components and also between the components themselves. Under ideal conditions, the more strongly bond ones displace the more weakly bond ones until all substances are focused into consecutive individual zones of pure substance that leave the column at the speed of the advancing displacer front in the order of the stationary phase affinities.

One of the important distinctions between displacement and elution mode chromatography is that, in displacement mode chromatography, the displacer front always remains behind the consecutive feed zones, while, in elution mode chromatography, the eluent or desorbent moves through the feed zones with the components to be separated.

The displacer is a unique feature of displacement mode chromatography. At the same time, the choice of the displacer has consequences not only for the success, but also for the economic soundness of the final method. Mathematical simulations, which take into account concentrations in the mobile and stationary phases, allow some predictions concerning the necessary displacer characters for a given substance mixture to be separated.

A displacement mode chromatography method for purifying proteins using, as a stationary phase, a cation-exchange resin and, as a displacer, a cationic species is disclosed in U.S. Pat. No. 5,478,924. These cationic species are poly(quaternary ammonium) salts having a dendritic framework formed by reiterative reaction sequences starting from pentaerythritol. Their structure consists, on the one hand, in a hydrophobic interior zone containing ramifications connected to the initial core pentaerythritol and, on the other hand, in a hydrophilic exterior surface region bearing the quaternary ammonium groups.

The first and second generation pentaerythritol-based dendrimers, all terminated with trimethylammonium groups, having respectively a molar mass of about 2,000 g/mol and 6,000 g/mol, are described as being effective for the purification of a two-protein mixture, i.e. α-chymotrypsinogen A and cytochrome C.

However, it is mentioned that, due to the presence of impurities in the first generation dendrimers contributing to the desorption of the proteins and depression of their isotherms, the cytochrome C zone is considerably less concentrated in relation to the α-chymotrypsinogen A zone.

The preparation of these poly(quaternary ammonium) salts is relatively tedious, time and cost consuming, involving low overall yield multi-step synthesis. The level of purity and homogeneity cannot be high, particularly for the high molar mass second generation pentaerythritol-based dendrimers.

It is also reported that the "zero" generation pentaerythritol-based dendrimers, terminated with trimethylammonium groups and having for instance a molecular weight of 620 g when X=Cl, are equally effective for the separation of the two proteins.

However, S. D. Gadam and S. M. Cramer have reported, in *Chromatographia*, 1994, 39, 409–18, that the behaviour of such low molar mass displacers depends to a much higher degree on the chromatographic conditions, for example the salt content of the mobile phase. As a consequence, the switch from displacer to elution promoter is more likely in the case of these substances.

One of the aims of the present invention is to provide a low molar mass polymer capable to be used as a cationic displacer, i.e. having high solubility in an aqueous carrier with a high binding tendency towards a cation-exchange stationary phase. This particular polymer has to be easily available on a large scale with high level of purity and homogeneity.

To this effect, the present invention relates to a linear water-soluble quaternary ammonium polymer having a homopolymeric chain of repeating unit of general formula (I):

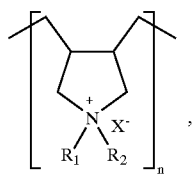

(I)

where each of $R_1$ and $R_2$ independently represents a member selected from the group consisting of linear or branched alkyl, hydroxyalkyl, alkoxyalkyl groups having from 1 to 6 carbon atoms, $X^-$ represents an anion, n is an integer comprised between 30 and 220. Furthermore, the polymer has a molar mass distribution of less than or equal to 1.5.

The anion represented by $X^-$ is selected from the group consisting of $F^-$, $Cl^-$, $Br^-$, $NO_3^-$, $OH^-$, $HSO_4^-$, ½ $SO_4^{2-}$, $CH_3COO^-$.

The preferred linear water-soluble quaternary ammonium polymer has the above general formula (I), where both $R_1$ and $R_2$ represent a methyl group and $X^-$ represents $Cl^-$, n being an integer comprised between 30 and 220. Such a preferred polymer has a number average molar mass comprised between about 4,800 g/mol and about 35,000 g/mol and a molar mass distribution of less than or equal to 1.5.

Since the 1950s, a number of preparations of linear water-soluble quaternary ammonium polymers having a homopolymeric chain of the same above-mentioned repeating unit have been described. They are based on polymerisation reactions employing various initiation methods, including radically, ionically, or X-ray induced polymerisation, and involving an alternating intra-intermolecular chain propagation.

However, most of these syntheses are oriented towards high molar mass polymers having a number average molar mass of up to 200,000 g/mol, or even more, with a conversion rate of more than 95%, which means that almost all the starting monomer is consumed in the course of the reaction. From these syntheses, result generally polymers having molar mass distributions greater than 3.

Such high molar mass polymers are produced, for example, using a technology as it is described in FR 2 448 546 and the classical polymerisation conditions to be applied to obtain such polymers are described for instance in J. Ulbricht, "*Grundlagen der Synthese von Polymeren*", 2nd edition, Huethig & Wepf, 1992. It is reported in this textbook that to produce low molar masses, one has to increase the free-radical polymerisation initiator concentration and/or the reaction temperature.

In the particular case of the polymerisation of diallyldimethylammonium chloride, H. Dautzenberg et al. report, in "*Polyelectrolytes: Fornation, characterisation and application*", Carl Hanser Verlag, Munich, 1994, p. 20, that increasing the initiator concentration and the temperature as proposed above leads to an increase of linear propagation with the consequence of pendent double bounds and in the following chain branching.

To obtain a linear polymer having a narrow molar mass distribution, the radically initiated polymerisation reaction is normally only to low conversion, i.e. less than 10%.

None of the existing preparations offers a method to obtain, without special fractionation, a poly(diallyldimethylammonium chloride)-type polymer having a low molar mass and a narrow molar mass distribution at conversions more than 40%.

Another of the aims of the present invention is to provide a method for the preparation of the polymer as defined above by the general formula (I) and having a molar mass distribution of less than or equal to 1.5.

To this effect, the present invention relates to a process for the preparation of the above mentioned polymer of general formula (I).

In this process, a quaternary ammonium monomer of general formula (II):

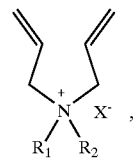

(II)

where each of $R_1$ and $R_2$ independently represents a member selected from the group consisting of linear or branched alkyl, hydroxyalkyl, alkoxyalkyl groups having from 1 to 6 carbon atoms and $X^-$ represents an anion;
is brought into contact with a catalytic amount of a free-radical polymerisation initiator in an oxygen-free aqueous reaction medium at a temperature comprised in the range of 30° C. and 70° C., said monomer being introduced into the reaction medium in such a way that its concentration in said reaction medium in the course of the polymerisation reaction is less than or equal to 3 mol/l.

Preferably, the anion represented by $X^-$ is selected from the group consisting of $F^-$, $Cl^-$, $Br^-$, $NO_3^-$, $OH^-$, $HSO_4^-$, ½ $SO_4^{2-}$, $CH_3COO^-$.

Preferably, the monomer is continuously introduced into the reaction medium in such a rate that its concentration in the reaction medium remains above the lower limit of 1 mol/l. More preferably, the monomer is continuously introduced into the reaction medium in order to maintain constant its concentration in the reaction medium.

Preferably, the reaction medium is maintained at a constant temperature.

The free-radical polymerisation initiator used in the process is a water soluble peroxy initiator. Preferably, this initiator is selected from the group consisting of ammonium peroxydisulfate, potassium peroxydisulfate, sodium peroxydisulfate, lithium peroxydisulfate. More preferably, the initiator is ammonium peroxydisulfate.

The free-radical polymerisation initiator is used as such. It does not require the use of any auxiliary agent such as metal sequestering agents.

The concentration of the free-radical polymerisation initiator in the reaction medium is comprised between $1.10^{-3}$ mol/l and $50.10^{-3}$ mol/l.

Furthermore, the reaction medium can be filtrated under ultrafiltration conditions in order to separate the obtained polymer from non-reacted monomer and initiator. The use of a membrane allowing a cut-off of 3,000 g/mol is appropriate.

In another aspect, the present invention relates to the use of the above mentioned polymer of general formula (I), as a cation-exchange displacer for a displacement mode chromatography method involving a cation-exchange stationary phase.

In a further aspect, the present invention relates to a method for separating biomolecules contained in a sample by using the above mentioned polymer of general formula (I). This method comprises:

i) passing said sample containing the biomolecules to be separated through cation-exchange stationary phase so that said biomolecules adsorb on said stationary phase;

ii) passing an aqueous solution of said polymer through said stationary phase so that the biomolecules to be separated are displaced by said polymer by displacement mode chromatography.

This method is appropriate for the separation of molecules bearing a permanent or temporary positive net-charge or positively charged patches, which enable them to interact with the cation-exchange stationary phase.

Such molecules, with the required above-mentioned electrolytic character, can be biomolecules, synthetic or semi-synthetic molecules such as amino-acids, peptides, proteins, nucleosides, nucleotides, polynucleotides, alkaloids, antibiotics, saccharides, polysaccharides, lipids, drugs, drugs candidates and derivatives thereof.

The appropriate stationary phase used in the method can be any type of weak or strong cation-exchange stationary phase. Such stationary phases can be those bearing on their surface carboxymethyl groups, sulphopropyl groups, methyl-sulphonate groups, phospho groups or any carboxylate and sulfo groups anchored by any other spacers, or other groups bearing permanent or pH-dependent negative charges. These stationary phases can also be stationary phases displaying a partial cation exchanger character, such as hydroxy- and fluoroapatite and mixed mode phases.

The aqueous solution of the polymer is prepared before passing through the stationary phase. This solution can eventually contain water-miscible organic solvents.

As the polymer is a quaternary ammonium salt, it can be considered as being not dependent on the pH. Therefore the aqueous solution and the mobile phase can be any buffer usually suitable for cation-exchange chromatography, including volatile buffer systems. Under certain circumstances, buffer usually suitable for anionic ion-exchange chromatography can also be used.

The preferred buffer substances are citric acid, acetic acid, 4-(2-hydroxyethyl)piperazine-1-ethanesulfonic acid (HEPES), N,N-bis(2-hydroxyethyl)glycine (BICINE), phosphate, $\alpha,\alpha,\alpha$-tris(hydroxymethyl)-methylamine (TRIS).

The following detailed description refers to the drawing where:

Considering the special features that should have a cationic displacer, one might think that polydiallyldimethylammonium could have been a good candidate. In particular, bearing permanent positive charges, one could expect it could bind to a cation-exchange stationary phase.

Polymers, obtained from diallyidimethylammonium chloride, are commercially available. These polymers have high, or very high, number average molar mass and/or large molar mass distribution. Unfortunately, as it will be demonstrated hereinafter using a polymer having a number average molar mass of 200,000 g/mol, they do not behave as a cationic displacer.

Therefore, there was a need for testing poly(diallyidimethylammonium chloride) having lower number average molar mass, for instance less than 35,000 g/mol, and a narrow molar mass distribution.

As none of the existing preparation methods is able to deliver the above-mentioned required polymers, one could think to separate them from the obtained mixture. However, such a purification is time and cost consuming and the level of purity remains low. Additionally, the products of these methods are not completely linear.

The process of preparation according to the present invention is a very efficient and straightforward way to get the required poly(diallyldimethylammonium chloride) having a number average molar mass comprised between 4,800 and 35,500 g/mol and a molar mass distribution of less or equal 1.5.

This process is based on the polymerisation of the monomer, i.e. diallyldimethylammonium chloride, initiated by a free-radical polymerisation initiator, i.e. ammonium peroxydisulfate, in an aqueous medium.

Diallyidimethylammonium chloride is a cheap and highly pure commercially available compound and a number of its analogues can be synthesised on a large scale.

To avoid branching, the process has to be run in such a way that the concentration of the monomer in the reaction medium is less than or equal to 3 mol/l.

Before the polymerisation reaction is initiated, an aqueous solution of the monomer at a concentration of 2 mol/l is placed into the reaction vessel. A sufficient amount of the initiator is added into this solution to initiate the reaction.

Figure 1:
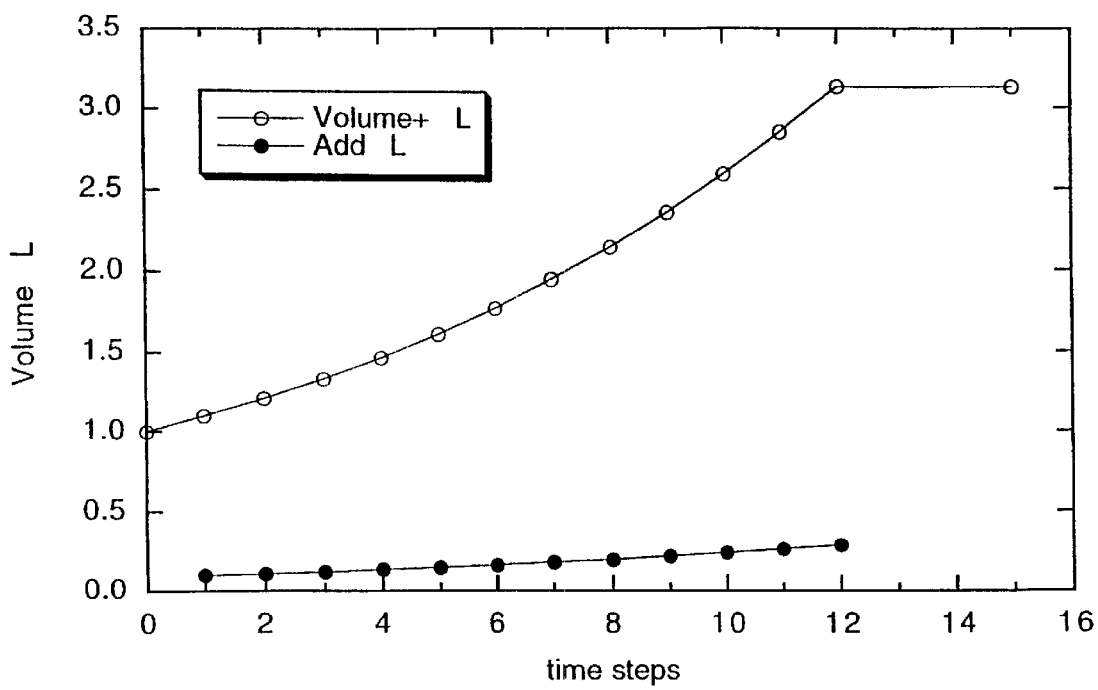
FIG. 1 represents the reaction medium volume change in the course of one embodiment of the process for the preparation of the polymer.

As the polymer is formed and the monomer consumed, a second monomer solution is continuously introduced, following the addition rate shown by the black circles on FIG. 1, into the reaction medium in order to maintain as constant as possible the monomer concentration in the reaction medium.

Figure 2:
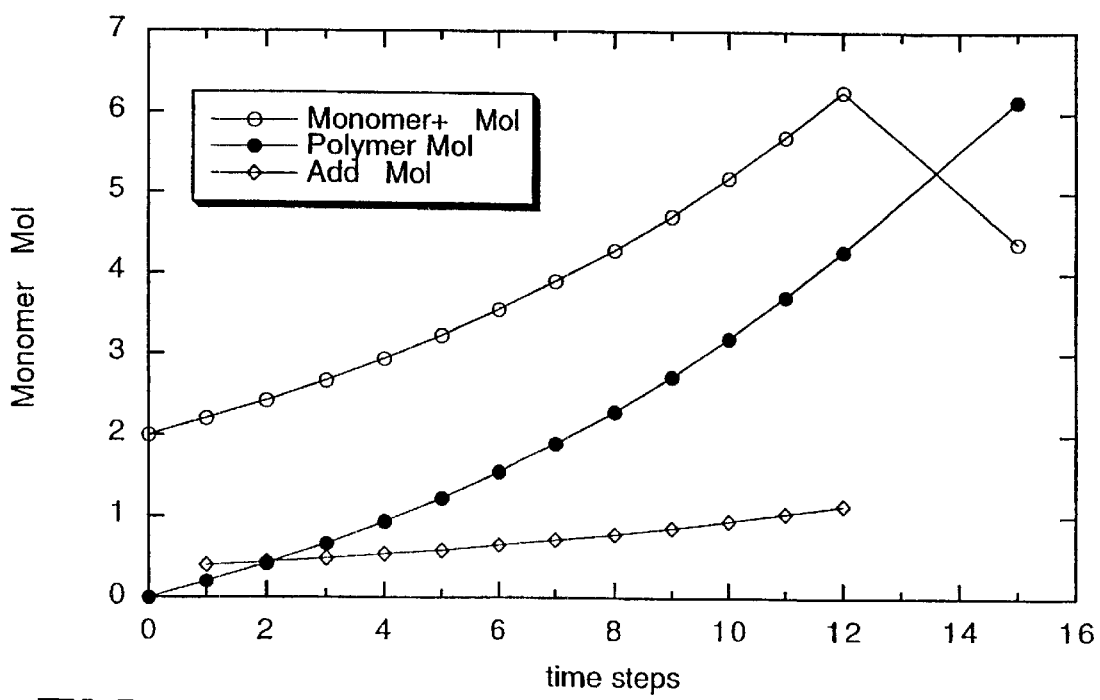
FIG. 2 represents the change of molar contents of the monomer and the polymer in the course of the same embodiment as for FIG. 1.

The reaction medium volume increases progressively (FIG. 1, white circles), as does the total molar contents of the components (FIG. 2).

Figure 3:
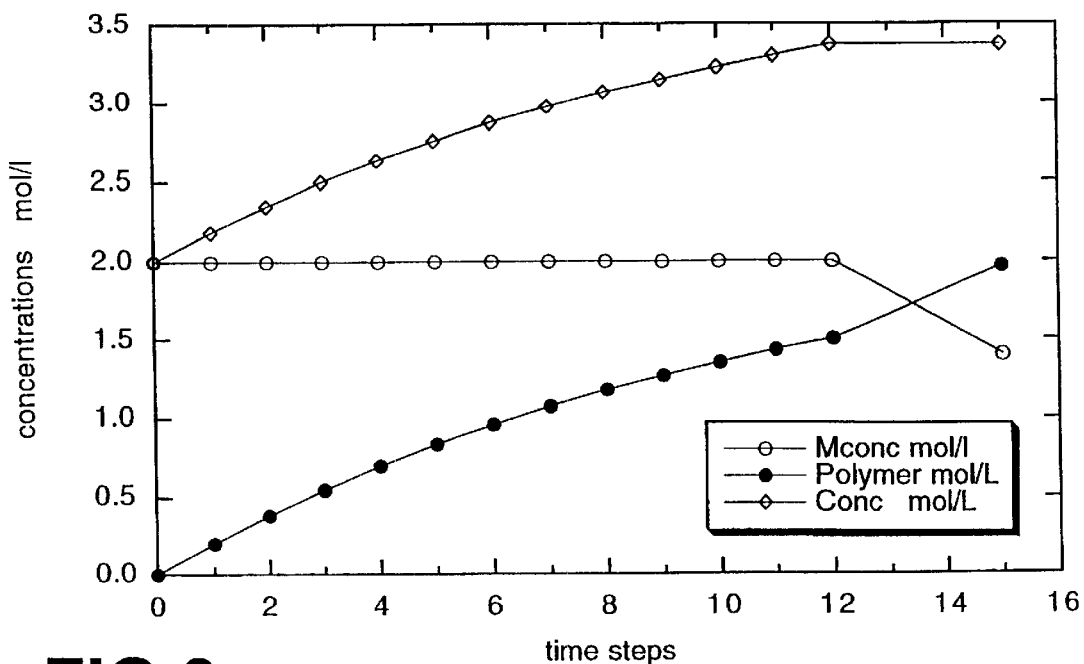
FIG. 3 represents the change of the concentrations of the monomer and polymer in the reaction medium in the course of the same embodiment as for FIG. 1.

As shown on FIG. 3, the monomer concentration remains constant as the polymer concentration increases.

Figure 5:
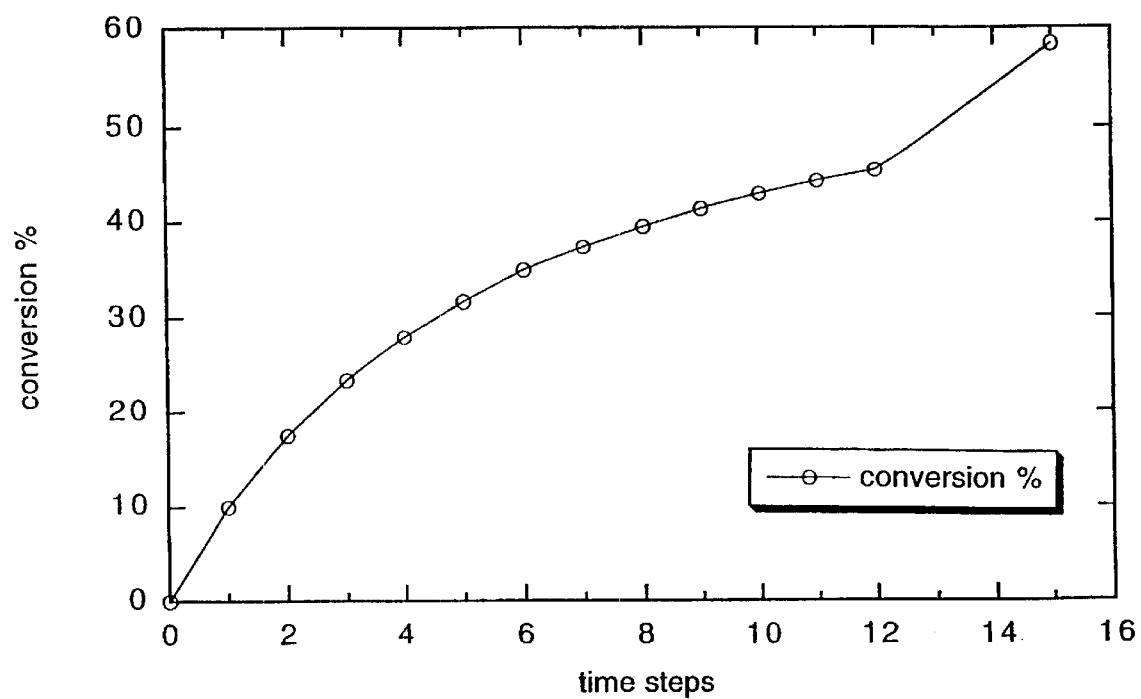
FIG. 5 represents the conversion rate in the course of the same embodiment as for FIG. 1.

As shown on FIG. 5, after a 24 hours time period of a continuous addition of monomer, the conversion rate is 45%. After 24 hours, the addition is stopped. The polymerisation continues and the conversion rate can be increased to values up to 60%.

The pure polymers, free of monomer, are obtained by filtration under ultrafiltration conditions using a membrane with a cut-off of 3,000 g/mol and the monomer can be recycled for further polymerisation reactions.

By modifying reaction parameters such as the monomer concentration in the reaction medium and/or the quantities of the initiator and/or the reaction temperature, polymers of various number average molar masses have been obtained.

For instance, when the initial monomer concentration is 3 mol/l, polymers having number average molar mass of 15,000, 18,000, 25,000 and 35,000 g/mol are obtained, and with an initial monomer concentration of 2 mol/l, polymers having a number average molar mass of 11,500, 14,000 and 18,000 g/mol are identified.

For each of these polymers, the molar mass distribution is always less than or equal 1.5.

The process of preparation of poly (diallyidimethylammonium chloride) offers several advantages.

As a one-pot preparation, involving cheap reagents, it is a very simple and economical process. The product can be obtained with a high level of purity by just performing an ultrafiltration.

Above all, it offers the possibility to prepare a large range of low number average molar mass polymers, having all a narrow molar mass distribution by just controlling the reaction parameters within the claimed ranges. For instance, by varying the monomer concentration and/or the free-radical initiator concentration and/or the reaction temperature, batches of polymer having number average molar masses respectively of 11,500, 14,000, 15,000, 18,000, 25,000 and 35,000 g/mol have been isolated, all having a molar mass distribution of less than or equal to 1.5.

Having all these low molar mass poly (diallyidimethylammonium chloride) in hand, their behaviour in a displacement mode ion-exchange chromatography method was considered and compared with a high molar mass poly(diallyidimethylammonium chloride). In particular, their ability to displace two proteins, i.e. cytochrome C and lysozyme, has been investigated.

Development of a displacement mode chromatography usually involves the following steps:
choosing the stationary phase;
optimising the mobile phase;
adjusting the column length to the sample size;
adjusting the flow rate;
finding a displacer.

Displacement mode chromatography is related to the relative affinities for the stationary phase between, on the one hand, the displacer and, on the other hand, the substances to be separated. Isotherms represent, for a selected stationary phase and a selected mobile phase, the relationship between the concentration of a particular component in the mobile phase and in the stationary phase.

Figure 6:
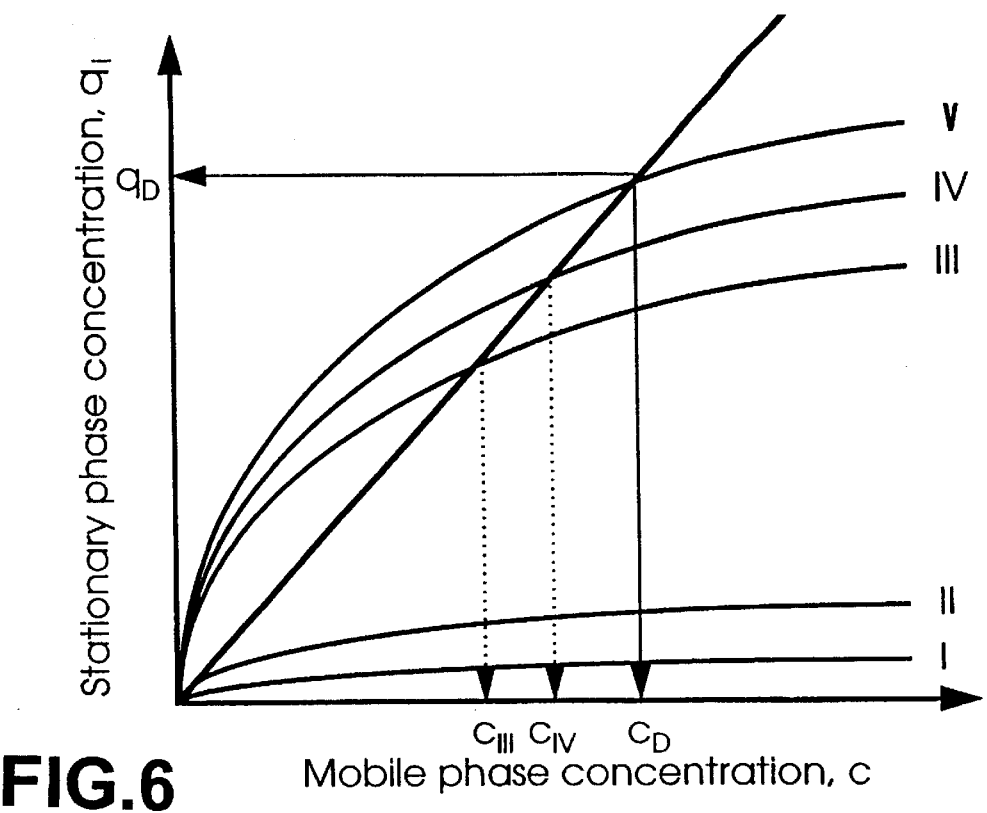
FIG. 6 is a schematic representation of isotherms characterising the components involved in a displacement mode chromatography method.

Such isotherm curves are schematically represented on FIG. 6. Five components have been considered. According to isotherm I, component I has the lowest affinity for the selected stationary phase while, according to isotherm V, component V shows the highest affinity. Therefore, component V could be considered as a displacer.

According to the mathematical simulation described by C. Horvath and A. Nahum in *J. Chromatogr.*, 1981, 218, 365–93, by choosing the displacer concentration $C_D$ in the mobile phase, all other concentrations in the substance zones are fixed. Their value can be taken from the intersection between the respective substance isotherms (i.e. isotherms III and IV) and an operating line linking the origin and the displacer concentration $C_D$ on the displacer's isotherm V. One can expect the substances IIII and IV to be displaced by the displacer, i.e. component V. Substances whose isotherms do not intersect with the operating line are classically eluted in front of the displacement train, these are for instance substances I and II.

Figure 7:
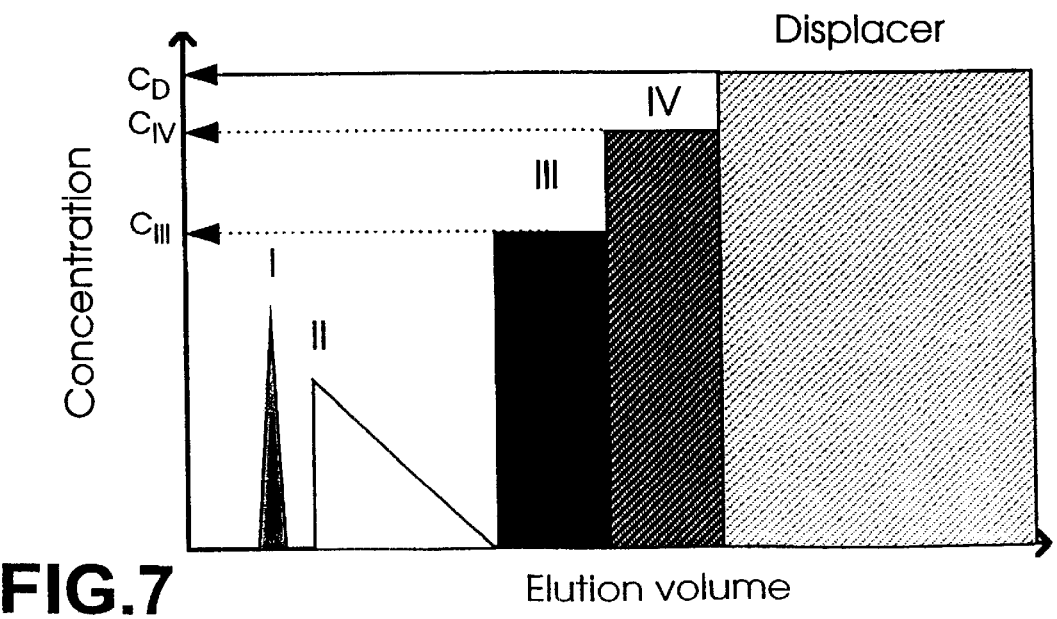
FIG. 7 is a schematic representation of a chromatogram obtained in a displacement mode chromatography method.

Under the ideal conditions assumed above, one can expect the chromatogram as shown on FIG. 7. The displacer pushes substance IV, which substance pushes substance III, while substances I and II are eluted in front of the displacement train. The borders between adjacent displaced zones are self-sharpening, hence their rectangular shape. In reality, dispersive effects such as diffusion, mass transfer resistance, extra column effects, counteract this self-sharpening. The overall result is a smoothing out of the sharp edges in the isotachic train, resulting in steep, but continuous concentration changes and some overlap between the zones.

Figure 8:
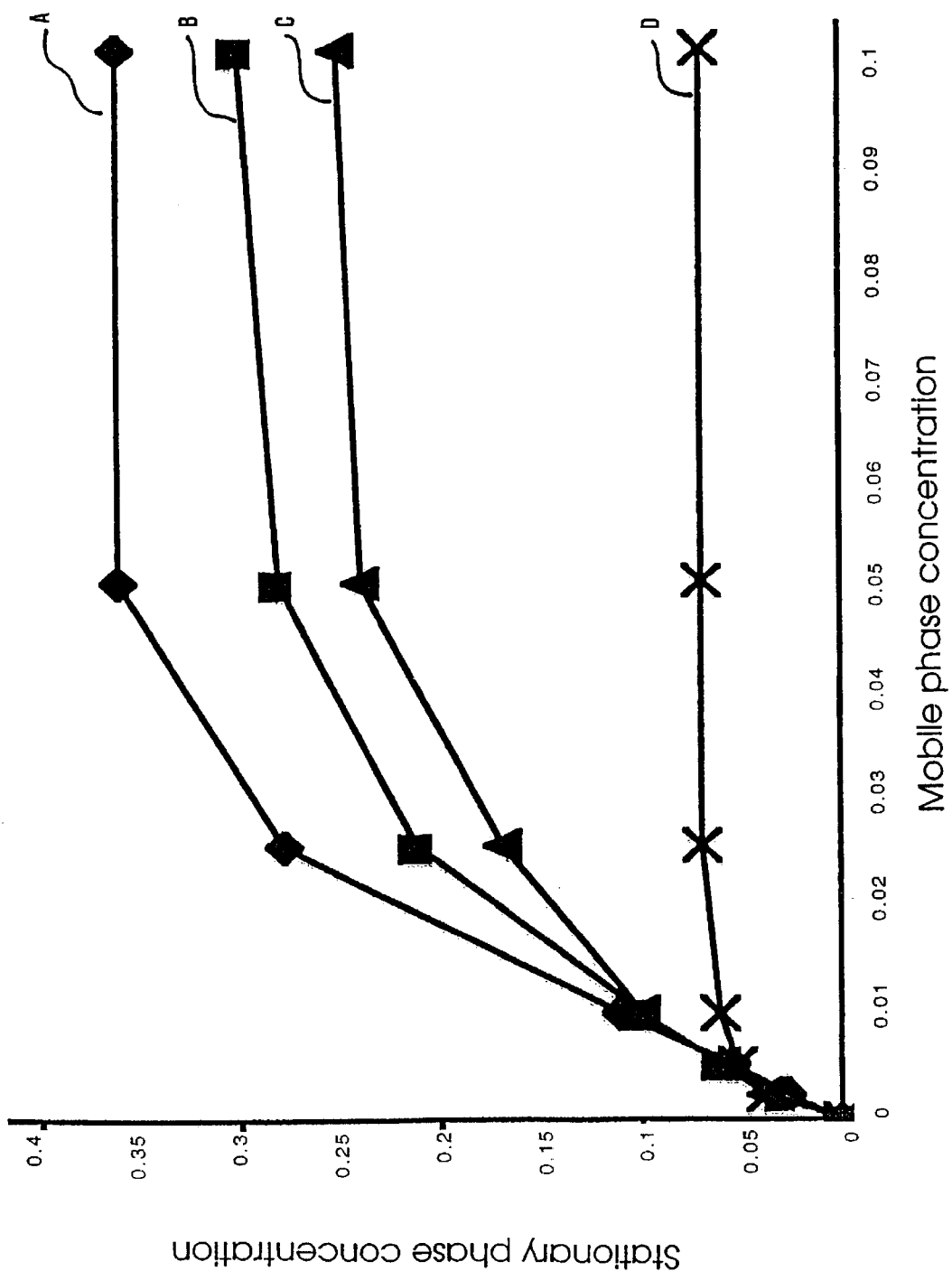
FIG. 8 represents isotherms of different components.

Thus, for applying such a mathematical prediction in order to find a appropriate displacer, among the poly (diallyidimethylammonium)-type polymers, for the separation of two proteins, four isotherms have been drawn on FIG. 8. Curve A and D correspond to the isotherms of two poly(diallyidimethylammonium chloride) having respectively a number average molar mass of 12,000 g/mol and a molar mass distribution of 1.5 and a number average molar mass of 200.000 g/mol and a molar mass distribution of 2.1. Curve B and C are the isotherms of two proteins, respectively lysozyme and cytochrome C. For such a measurement, the stationary phase is a cation-exchanger, i.e. UNO® and the mobile phase is pH 7.2 phosphate buffer.

Poly(diallyidimethylammonium chloride) having a number average molar mass of 12,000 g/mol and a molar mass distribution of 1.5 presents the higher affinity for the stationary phase while poly(diallyldimethylammonium chloride) having respectively a number average molar mass of 200,000 g/mol and a molar mass distribution of 2.1 has the lower affinity. By drawing the operating line as mentioned above, one can predict that the low molar mass polymer is able to displace lysozyme, which lysozyme is able to push cytochrome C. The high molar mass-polymer cannot be considered as a displacer.

Figure 9:
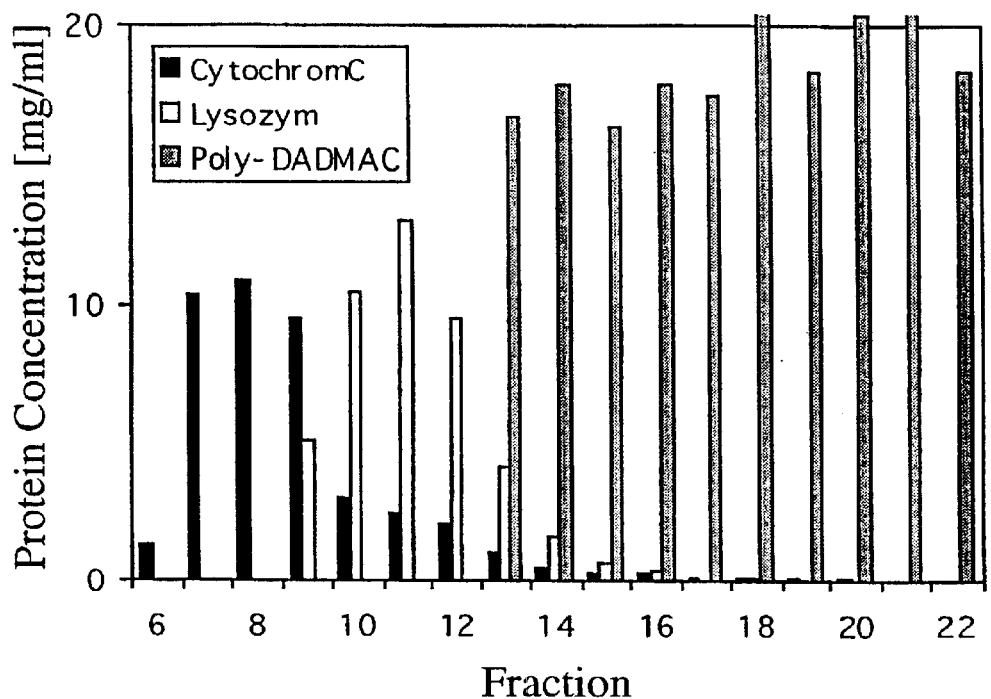
FIG. 9 is a chromatogram obtained by applying the method of separation.

These predictions are confirmed by running experiments. A sample containing both the proteins was adsorbed on the cation-exchanger. Then an aqueous solution of the low molar mass polymer was flushed through the stationary phase. FIG. 9 represents the obtained chromatogram. Cytochrome C was separated from lysozyme and obtained in a highly pure and concentrated form in the first fractions. Lysozyme was then collected with trace of cytochrome C on the front of the polymer, said polymer appearing with a rectangular shape.

Figure 10:
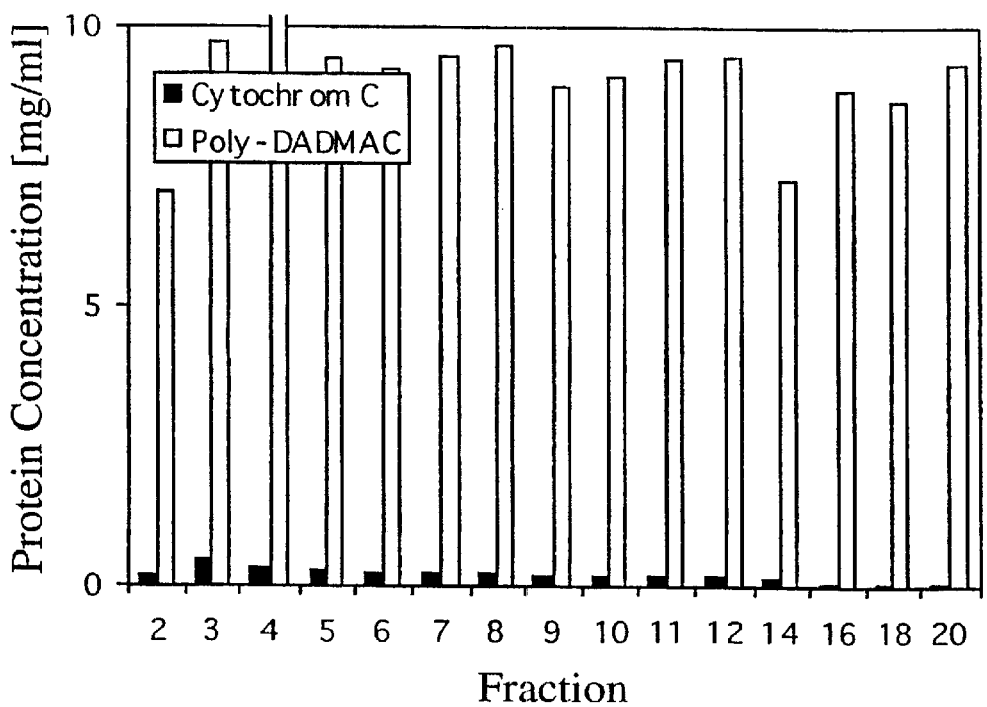
FIG. 10 is a chromatogram obtained with a comparative experiment using a high molar mass polymer.

In a second experiment, only cytochrome C was adsorbed on the stationary phase while a aqueous solution of the high molar mass polymer was flushed through the column. FIG. 10 represents the obtained chromatogram. As predicted from the isotherms, the protein was not displaced by the high molar mass polymer. A small amount of the adsorbed protein elutes in the polymer zone.

Similar investigations have shown that low molar mass poly(diallyidimethylammonium chloride) having a number average molar mass comprised between 4,850 and 35,500 g/mol and each a molar mass distribution of 1.5 are excellent displacers, in particular for the two above-mentioned proteins.

This remarkable behaviour is due, for one part, to the particular structure of the polymer having a limited number of repeating units placed on regular distance along the chain, each containing pH-independent permanent positively charged ammonium group, and, for the other part, to the high level of purity and homogeneity that can offer the process of preparation of these polymers.

In order to more illustrate the nature of the invention and the manner of practising the same, the following Examples are presented.

EXAMPLE 1

A 5 l reactor, equipped with stirrer, gas inlet, and a programmable pump, is filled with 1 l of a first monomer solution having a concentration of 2 mol/l (323 g DADMAC). The monomer solution is commercially available from Aldrich and is used as delivered (purum quality, purity>97%, pH<6.5).

Following a purge with $N_2$ at 50° C., 4.4 g of the initiator, dissolved in water, is added to start the polymerisation.

Related to the polymerisation rate, a second aqueous solution, purged with $N_2$ and kept below 30° C., containing the monomer with a concentration of 4 mol/l and an appropriate amount of the initiator is continuously added to the reactor as described below.

As shown on FIG. 1, the polymerisation starts with 1 l. The volume (white circles) increases progressively resulting from the increasing increments of the added monomer/initiator solution (black circles). After 24 h the polymerisation continues without further addition. (In FIGS. 1 to 5, the duration of one time step is 2 h).

As shown on FIG. 2, at the beginning of the polymerisation, the solution contains 2 mol of the monomer (white circles) and no polymer (black circles). During the first phase, quantities of both the monomer and the polymer increase in the reactor. Additionally, the increasing amount of added monomer is shown in the graph (white squares). During the second phase the polymer further increases whereas the monomer decreases.

As shown on FIG. 3, during the first phase, the polymer (black circles) and the total concentrations (white squares) increase. As the volume of the reaction medium (FIG. 1) and the quantity of the monomer (FIG. 2) increase, the monomer concentration (white circles) remains constant at 2 mol/l. During the second phase, the total concentration remains constant. The polymer concentration increases in the same way as the monomer concentration decreases.

Figure 4:
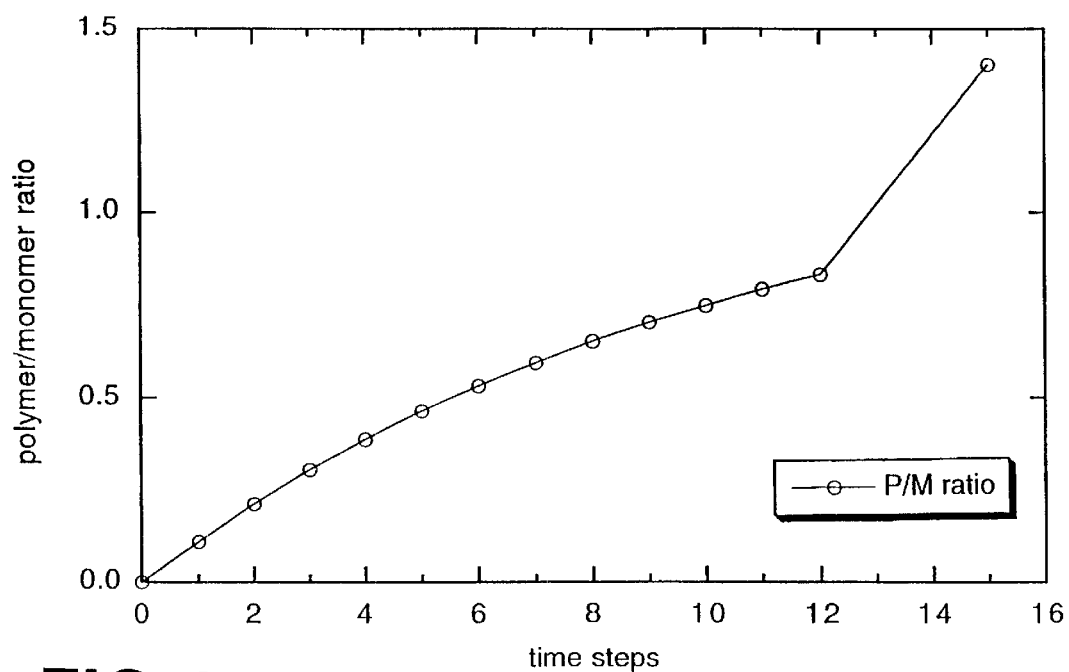
FIG. 4 represents the change of the polymer/monomer ratio in the course of the same embodiment as for FIG. 1.

As shown on FIG. 4, resulting from the constancy of the monomer concentration and the increasing polymer concentration, the polymer/monomer ratio changes.

FIG. 5 shows another way to express the change of the polymer/monomer ratio, the polymerisation conversion.

For the given example, the addition of the monomer was finished after 24 h. The polymerisation is continued for 6 h without addition of monomer. After 30 h, the monomer concentration in the reaction medium has reached the lower limit of 1.4 mol/l and 995 g of the polymer are received. This corresponds to a conversion of 58.4%.

The residual monomer and initiator are removed by ultrafiltration using a membrane having a cut-off of 3,000 g/mol. Following this purification, the solid polymer having a residual water content between 5 and 20% can be received by freeze drying.

Number average molar mass is determined by membrane osmometry and molar mass distribution by analytical ultracentrifugation measurements according to the methods described by C. Wandrey et al. in *Acta Polym.*, 1990, 41, 479–84, and in *Acta Polym.*, 1992, 43, 320–6.

By dilution viscosimetry in 1.0 N NaCl aqueous solution, an intrinsic viscosity $[\eta]=0.25$ dl/g was determined. This corresponds to a number average molar mass of $M_n=12,000$ g/mol. Molar mass distribution: $M_w/M_n=1.5$.

EXAMPLE 2

Procedure and equipment are the same as described for Example 1. However, the addition of the monomerrinitiator was extended to 30 h. After 36 h, 1430 g of the polymer were received. This corresponds to a conversion of 60.3%.

Number average molar mass of $M_n=12,000$ g/mol. The product quality was comparable to that of the product of Example 1.

EXAMPLES 3–5

Procedure and equipment are the same as described for Example 1. The different parameters are related in Table 1

TABLE 1

| Example | Monomer concentration mol/l | Initiator g | Time step h | $M_n$ |
|---------|---|---|---|---|
| 3 | 2 | 1.1 | 5.5 | 18,000 |
| 4 | 3 | 2.2 | 0.7 | 18,000 |
| 5 | 3 | 0.4 | 3.75 | 35,000 |

EXAMPLE 6

Comparative Example

In order to illustrate the effect of the monomer concentration on the number average molar mass, two polymerisations, only different in monomer concentration, were carried out. The monomer concentrations were 2 and 4 mol/l.

80 ml of an aqueous diallyldimethylammonium chloride (DADMAC) solution having a monomer concentration of either 2 or 4 mol/l are polymerised in a reactor which is equipped with stirrer, and gas inlet. At 50° C., $O_2$ is removed by flushing with $N_2$ for one hour. The polymerisation is started by addition of 350 mg ammonium peroxi-disulfate predissolved in 2 ml water.

a) Monomer concentration of 2 mol/l: after 5 h at 50° C., the polymerisation is stopped by dilution by addition of 80 ml water. Conversion 25%. Resulting product: $[\eta]=0.24$ dl/g; $M_n=11,500$ g/mol; $M_w/M_n=1.5$.

b) Monomer concentration of 4 mol/l: after 1 h at 50° C., the polymerisation is stopped by dilution by addition of 80 ml water. Conversion 36%. Resulting product: $[\eta]=0.74$ dl/g; $M_n=46,000$ g/mol.

These results show that, as the monomer concentration increases, the polymerisation reaction goes faster, but the number average molar mass passes from 11,500 to 46,000 g/mol.

EXAMPLE 7

Comparative Example

In order to decrease the number average molar mass when using a monomer concentration of 4 mol/l, the classical polymerisation conditions were applied. Thus, the temperature and the initiator concentration were increased.

Procedure and equipment are the same as described for Example 6. However, the monomer concentration was 4 mol/l and 700 mg of the initiator were added. The duration of the polymerisation was 15 min. The reaction temperature was 70° C. Conversion 81%. Resulting product: [η]=0.35 dl/g, $M_n$=18,000 g/mol, molar mass distribution about 3.5.

These results show that the polymerisation rate becomes very high, only after a very short time of 15 min. At these high conversions, the number average molar mass is relatively low but always products with broad molar mass distributions are obtained.

Application Example A

A fluid, consisting in a 0.005 M sodium phosphate buffer at pH 7.2, was stored in a container connected to a HPLC pump 64 manufactured by ERC, Alterglofsheim, Germany. The pump pumped the fluid at a flow rate of 0.2 ml/min to a chromatography column charged with a strong cation-exchanger [UNO® S1 (7×35 mm, 1.3 ml, Bio-Rad)]. The effluent from the column flowed to a fraction collector which separates the effluent on either a volume or time basis.

A sample containing 3.4 mg of cytochrome C and 3.5 mg of lysozyme was injected through the column via a 1 ml loop. Then a 1.8 M buffered solution of the displacer, consisting of a poly(diallyldimethylammonium chloride) having a number average molar mass of 12,000 g/mol and a molar mass distribution of 1.5, was injected through the column via a 5 ml preparative loop.

For the regeneration of the column, a 0.005 M phosphate buffer, containing 1 M sodium chloride, was used.

The displacement mode chromatography was monitored by collecting samples twice per minutes and the samples were analysed by analytical HPLC as described by R. Freitag and J. Breier, *J. Chromatogr.*, 1995, 691, 101.

As shown on FIG. 9, the separation between the two proteins is excellent. Cytochrome C was collected first in fractions 6 to 9 with a very high level of purity. Then, lysozyme is collected in fractions 10 to 12 with an excellent level of purity. The displacer front is sharp. The displacer appeared in fraction 13 with traces of the proteins.

Application Example B

Procedure and equipment are the same as described for Application Example A. However, the chromatography column was replaced by a Bio-Scale S2 column (7×52 mm, 2 ml, 10 μm porous particles, Bio-Rad).

The two proteins were obtained with a similar quality as for example A and the displacer front was still sharp.

Application Example C

Comparative Example

The following example illustrates the importance of relative affinities for the stationary phase to differentiate displacement mode chromatography from elution mode chromatography and shows that only polydiallyldimethylammonium having low molar masses can be consider as displacer.

The same equipment as for Application Example A was used. A sample containing only one protein, i.e. 2.9 mg of cytochrome C, was injected in the column. Then a 1.8 M buffered solution of a poly(diallyldimethyl-ammonium chloride) having a number average molar mass of 200,000 g/mol and a molar mass distribution of 2.1 was passed through the column. Fractionation and analysis followed the same procedure as for Application Example A.

As shown on FIG. 10, both the protein and the polymer were collected in the same fractions from fraction 2 till fraction 20. The polymer did not play at all the role of displacer.

The behaviour of this polymer is to be expected from the recorded isotherms on FIG. 8. Here the isotherms for the high molar mass poly(diallyldimethylammonium chloride) are much lower than those for polymers with a similar chemical framework but lower average molar mass.

Thus, polymers of poly(diallyldimethylammonium chloride) type, having an number average molar mass below ca. 35,000 g/mol, are excellent candidates to be used as cationic displacer in displacement mode chromatography, whereas polymers of the same type, but having a much higher number average molar mass are not.

What is claimed is:

1. A linear water-soluble quaternary ammonium polymer having a homopolymeric chain of repeating unit of general formula (I):

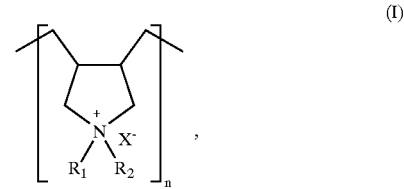

where each of $R_1$ and $R_2$ independently represents a member selected from the group consisting of linear or branched alkyl, hydroxyalkyl, alkoxyalkyl groups having from 1 to 6 carbon atoms, $X^-$ represents an anion and n is an integer comprised between 30 and 220, said polymer having a molar mass distribution of less than or equal to 1.5.

2. The polymer according to claim 1, characterised in that $X^-$) represents an anion selected from the group consisting of $F^-$, $Cl^-$, $Br^-$, $NO_3^-$, $OH^-$, $HSO^{4-}$, ½ $SO_4^{2-}$, $CH_3COO^-$.

3. The polymer according to claim 2, characterised in that both $R_1$ and $R_2$ represent a methyl group and $X^-$ represents $Cl^-$.

4. A process for the preparation of the polymer of claim 1, characterised in that a quaternary ammonium monomer of general formula (II):

where each of $R_1$ and $R_2$ independently represents a member selected from the group consisting of linear or branched alkyl, hydroxyalkyl, alkoxyalkyl groups having from 1 to 6 carbon atoms and $X^-$ represents an anion;

is brought into contact with a catalytic amount of a free-radical polymerisation initiator in an oxygen-free aqueous reaction medium at a temperature comprised in the range of 30° C. and 70° C., said monomer being introduced into the reaction medium in such a way that its concentration in said reaction medium in the course of the polymerisation reaction is less than or equal to 3 mol/l.

5. The process according to claim 4, characterised in that said monomer is continuously introduced into the reaction medium in such a rate that the concentration of said monomer in the reaction medium remains above 1 mol/l.

6. The process according to claim 5, characterised in that said monomer concentration remains constant.

7. The process according to claim 6, characterised in that the reaction medium temperature is maintained constant.

8. The process according to claim 7, characterised in that said free-radical polymerisation initiator is a water soluble peroxy initiator and in that the concentration of said initiator in the reaction medium is comprised between $1.10^{-3}$ mol/l and $50.10^{-3}$ mol/l.

9. The process according to claim 8, characterised in that furthermore said reaction medium is filtrated under ultrafiltration conditions in order to separate the obtained polymer from non-reacted monomer and initiator.

10. An improved displacement mode chromatography method involving a cation-exchange stationary phase and a cationic displacer, wherein the improvement comprises selecting a polymer as claimed in claim 1 as said cationic displacer.

11. A method for separating biomolecules contained in a sample by using the polymer of claim 1, comprising:
  i) passing said sample containing the biomolecules to be separated through cation-exchange stationary phase so that said biomolecules adsorb on said stationary phase;
  ii) passing an aqueous solution of said polymer through said stationary phase so that the biomolecules to be separated are displaced by said polymer by displacement mode chromatography.

* * * * *

UNITED STATES PATENT AND TRADEMARK OFFICE
CERTIFICATE OF CORRECTION

PATENT NO. : 6,489,421 B1
DATED : December 3, 2002
INVENTOR(S) : Ruth Freitag and Christine Wandrey It is certified that error appears in the above-identified patent and that said Letters Patent is hereby corrected as shown below:

Column 2,
Line 51, please delete "39" and insert in lieu thereof -- 39 --.

Column 3,
Line 52, please delete "Fornation" and insert in lieu thereof -- Formation --.

Column 7,
Line 55, please delete "218" and insert in lieu thereof -- 218 --.
Line 62, please delete "IIII" and insert in lieu thereof -- III --.

Column 8,
Lines 18, 27 and 59, please delete "diallyidimethylammonium" and insert in lieu thereof
-- diallyldimethylammonium --.

Column 10,
Line 4, please delete "41" and insert in lieu thereof -- 41 --.
Line 5, please delete "43" and insert in lieu thereof -- 43 --.
Line 13, please delete "monomerrinitiator" and insert in lieu thereof
-- monomer/initiator --.

Column 11,
Lines 30 and 66, please delete "diallyidimethylammonium" and insert in lieu thereof
-- diallyldimethylammonium --.
Line 41, please delete "691" and insert in lieu thereof -- 691 --.

UNITED STATES PATENT AND TRADEMARK OFFICE
CERTIFICATE OF CORRECTION

PATENT NO. : 6,489,421 B1
DATED : December 3, 2002
INVENTOR(S) : Ruth Freitag and Christine Wandrey It is certified that error appears in the above-identified patent and that said Letters Patent is hereby corrected as shown below:

<u>Column 12,</u>
Line 4, please delete "diallyldimethyl-ammonium" and insert in lieu thereof
-- diallyldimethylammonium --.
Line 16, please delete "diallyidimethylammonium" and insert in lieu thereof
-- diallyldimethylammonium --.
Line 46, please delete "X$^-$)" and insert in lieu thereof -- X$^-$ --.
Line 47, please delete "HSO$^{4-}$" and insert in lieu thereof -- HSO$_4^-$ --.

Signed and Sealed this

Sixth Day of May, 2003

JAMES E. ROGAN
*Director of the United States Patent and Trademark Office*